United States Patent [19]

Orrell et al.

[11] 4,103,700
[45] Aug. 1, 1978

[54] AVIATION FUEL GRADE MONITOR

[75] Inventors: Leonard Orrell, Warrington; John Whittle, Upton, both of England

[73] Assignee: Shell Oil Company, Houston, Tex.

[21] Appl. No.: 773,997

[22] Filed: Mar. 3, 1977

[30] Foreign Application Priority Data

Mar. 16, 1976 [GB] United Kingdom ............... 10504/76

[51] Int. Cl.² ........................................... F16K 31/28
[52] U.S. Cl. ................................... 137/172; 137/202; 137/423; 73/440
[58] Field of Search ............... 137/172, 202, 192, 423, 137/491; 73/440

[56] References Cited

U.S. PATENT DOCUMENTS

| | | | |
|---|---|---|---|
| 2,162,326 | 6/1939 | Cooper | 137/172 X |
| 2,594,105 | 4/1952 | Watts | 137/172 |
| 2,842,152 | 7/1958 | Winter | 137/172 X |
| 3,958,591 | 5/1976 | Hansel | 137/202 |

FOREIGN PATENT DOCUMENTS 1,528,000  4/1968  France ........................ 73/440

*Primary Examiner*—Alan Cohan

[57] ABSTRACT

A method and apparatus for monitoring the density of a flowing fluid and controlling the flow thereof. The apparatus comprises at least one vertical tube, having an inlet at the bottom and an outlet at the top for establishing a fluid flow through the tube. A movable member, having a weight to volume ratio substantially equal to the density of the fluid, is disposed to move freely in the tube between the inlet and outlet, and adapted to close either the inlet or outlet when the density deviates substantially from said ratio. Closing of the inlet or outlet is used to stop the fluid flow.

6 Claims, 5 Drawing Figures

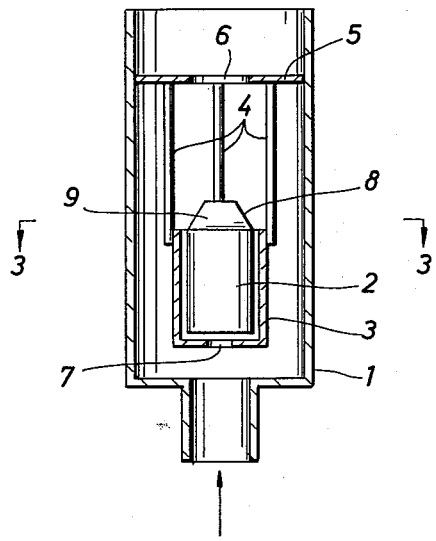
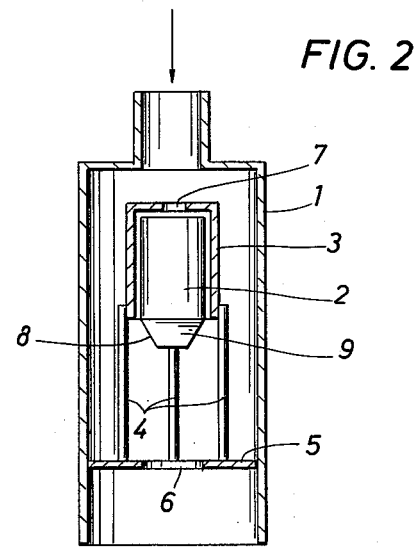
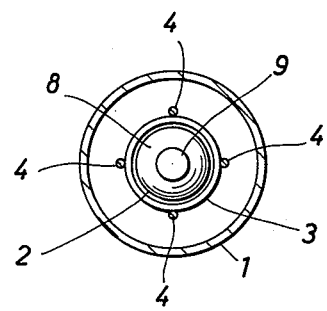
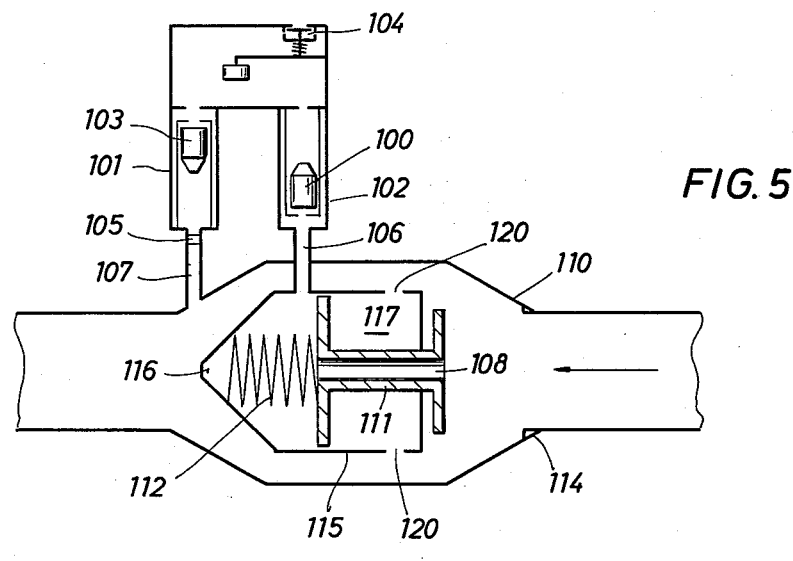

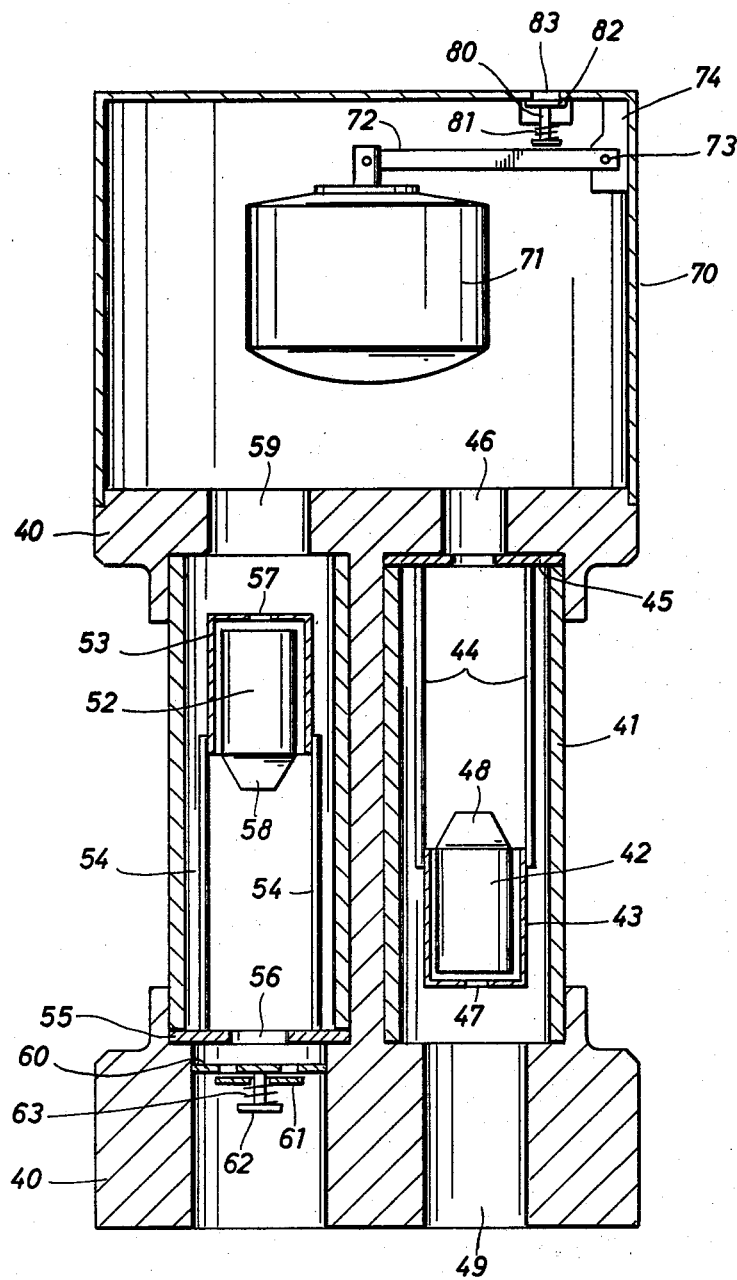

AVIATION FUEL GRADE MONITOR

BACKGROUND OF THE INVENTION

The present invention relates to an apparatus for monitoring changes in density of a flowing liquid and responding thereto, as well as to a system for preventing the passage of a liquid with a density above or below a predetermined value or outside a predetermined range.

Bulk transportation of liquids is a very important factor in today's industrial scene. For example, crude oil is often transported long distances from a wellhead through a pipeline to a sea tanker, which sea tanker then transports the crude oil further to the storage tanks of a refinery. At the refinery the crude oil passes through many processes before it finally emerges as refined products. These products are then transported either in road, rail or sea tankers, or through product pipelines, to distribution depots or direct to the storage facilities of bulk users. Examples of such bulk users are power stations, factories, chemical conversion plants, transport companies and air fields. The process, as described above, is basically a continuous closed one with products having to be transported away from the refinery quickly so that more crude oil can be accepted and processed. Pumping and flow rates are often quite high. Flow rates in excess of 200 gallons per minute are usual and can often be in excess of 1,000 gallons per minute.

Materials having very different purposes, for example aviation gasoline and aviation turbine fuel, which if incorrectly identified or if cross-contaminated could result in potentially hazardous situations, often superficially resemble each other and are difficult to distinguish—most especially in closed systems at high flow rates. A further example of potentially hazardous cross-contamination is of gasoline with kerosine, paraffin, diesel fuel oil supplied in bulk to storage depots or bulk users.

The examples given above are of hydrocarbon materials, and in particular, of those hydrocarbon materials most often used as fuels. This is because with these materials there is perhaps the greatest change of cross-contamination which could produce situations which may be potentially hazardous. It will be understood, however, that there are many liquids other than hydrocarbon fuels which are transported in bulk, and where the possibility of cross-contamination or incorrect identification can exist, such a happening producing undesirable results even if not potentially hazardous.

At high flow rates, and especially in the closed type of system discussed, swift detection of off-specification material is very important since action must be taken as soon as possible to halt the flow of material or at least to divert it to a different path.

A number of apparatus exist for identification of the various liquids most often handled in bulk but most of these are highly sophisticated, comprise expensive, easily damaged parts, and need to be operated by trained operators, or they do not work sufficiently quick at the high flow rates involved.

Thus, a need exists for an apparatus for monitoring changes in density of a flowing liquid which apparatus is operable at high flow rates, is simple and robust, and which is reliable. The present invention provides such an apparatus.

BRIEF SUMMARY OF THE INVENTION

According to the present invention, an apparatus for monitoring the density of a flowing liquid and for controlling the flow thereof, comprises a body having an inlet and an outlet, and adapted for the passage of said liquid therethrough, and a movable member having a weight/volume ratio substantially equal to said density which member is adapted to move freely within said body between its outlet and its inlet, and is also adapted sealingly to engage with either said inlet or said outlet.

If an apparatus, according to the present invention, is used in a system for preventing the passage of a liquid with a density above a predetermined value, the body, which advantageously is of tubular shape, is preferably placed in a substantially vertical position whereby a flow of liquid is made to pass through the body, for example in an upward direction, and the movable member (also referred to hereinafter, for convenience, as a float) is adapted to maintain a substantially constant position within the body, while the density of the flowing liquid does not increase far beyond the predetermined value, but to rise in response to a sufficiently large increase in density of the flowing liquid, causing the float to close off the outlet of the body. The float will be held up into the exit by the pressure of the liquid within the vertical body as well as by its own buoyancy. A decrease in the density of the flowing liquid will cause the float to sink within the vertical body. However, because of the force of liquid flowing into the body through the inlet, the float cannot move into and close off the latter.

In order to prevent the closure of the inlet under all circumstances, the apparatus, according to the invention, comprises preferably inside the body a guide construction for the float in such a manner that the float cannot engage with the inlet.

The ability of the float to maintain a substantially constant position within the vertical body, while the density of the flowing liquid remains substantially within the predetermined range, but to move into and sealingly engage with the exit from the body in response to a change outside the predetermined range, is influenced by temperature/density variations within the flowing liquid, the design of the float and the thermal coefficient of the expansion of the material from which the float is fabricated. In most situations where it is envisaged that apparatus, according to this invention, will be employed, it is unlikely that very large liquid temperature differences will be encountered; however, it is advisable that the material used for the float and its design are selected to compensate for whatever differences there might be. If very large differences are likely, more than one float can be prepared and the most suitable one employed at any time. Alternatively, it will be possible to increase the weight of the float by adding weights thereto.

A preferred apparatus, according to the present invention, comprises two floats, each being adapted to move freely in a separate part of the tube, each part having its own inlet and outlet, while the outlet of the first part communicates with the inlet of the second part.

It will be understood that the two separate parts of the tube shall not necessarily mean that the tube should be made in one piece; it will be shown that the tube may in principle comprise three parts, i.e., a first piece of tube, a chamber, and a second piece of tube.

This preferred embodiment of the apparatus, according to the invention, may be applied in a system for preventing the passage of a liquid with a density outside a predetermined range. The separate parts of the tube are, for example, placed in a vertical position. The flowing liquid can pass through the combination of vertical tubes in either order, although for reasons explained later, we prefer the flowing liquid to flow upwardly in the first vertical tube. Such a system enables changes in density of a flowing liquid outside of a predetermined range to be recognized and the flow of liquid through the system to be halted when either of the predetermined ranges are exceeded.

The system of the present invention, as discussed so far, monitors changes in the density of a flowing liquid and responds to them by halting the flow of liquid through itself. This response can be employed further. For example, only a proportion of the main flow of liquid need pass through the apparatus, and the response of the latter can be employed to halt or divert the main flow. This can be achieved, for example by placing the apparatus in the actuating line of a servo-operated valve when halting of the flow through the apparatus, and thus, the actuating line will cause the main valve to shut off. Either the apparatus or the main valve can further be connected to means for diverting the main liquid flow.

By the provision of suitable monitoring means, for example electrical contacts on the float and/or either the guide construction or the inlet or outlet, the position of the float within the tube can be monitored and responded to, for example by the operation of a shutoff or diverting valve.

If the flow rate of the flowing liquid is relatively low, the whole of the flow liquid can safely be passed through an apparatus, according to the invention, but it is preferred, especially at flow rates in excess of 200 gallons per minute, that only a representative proportion of the main flow be passed through. In an especially preferred embodiment of the invention, a representative flow of about 0.1% to 1.0% of the main flow is passed through an apparatus, according to the invention, and the halting of this flow of liquid is used to operate a servo-assisted valve in the main flow. We have found that combination of an apparatus, according to this invention, with one of the commercially available servo-assisted valves operated by switching a side flow taken through the body of the valve piston from the main flow, for example the Cobham Servo Control Valve, Type SV., manufactured by Alan Cobham Engineering Limited of Great Britian, to be particularly useful.

BRIEF DESCRIPTION OF THE DRAWINGS

The invention will now be described by way of example with reference to the accompanying drawings, in which:

FIG. 1 shows a diagrammatic cross-sectional view of an apparatus comprising a single vertical tube through which liquid flows upwardly;

FIG. 2 shows a diagrammatic cross-sectional view of a second apparatus comprising a single vertical tube which liquid flows downwardly;

FIG. 3 shows a diagrammatic cross-sectional view of the apparatus shown in FIG. 1, taken along with the line A—A$^1$;

FIG. 4 shows a diagrammatic cross-sectional view of a preferred apparatus comprising a combination of the two apparatuses shown in the FIGS. 1 and 2;

FIG. 5 shows a diagrammatic cross-sectional view of an especially preferred combination of the apparatus of FIG. 4, with servo-operated valve.

Referring to FIG. 1, a vertical tube 1, preferably made of glass or some other transparent material to facilitate determination of the position of the float, contains a float 2, seated loosely with a basket 3. The basket 3 is suspended by means of a series of connecting/guide rods 4, from a horizontal disc 5, which sealingly contacts the inner periphery of the tube 1 at or near its exit, and which has a central hole 6 which functions as the exit orifice or outlet from the tube 1. A small hole 7 is provided in the base of the basket 3 to allow liquid to enter when the float 2 moves upwardly within it. In order to provide a good seal between the float 2 and the exit orifice 6, the side walls 8 of the upper section 9 of the float 2 are chamfered inwardly towards the top. Liquid flowing upwardly through the tube 1 in the direction of the arrow will, if its density is within the predetermined range, flow round the basket 3, over the chamfered side walls 8 of the float 2, between the connecting/guide rods 4, and out through the exit orifice 6. The float 2 will remain seated within the basket 3. If a liquid, the density of which is greater than the predetermined range, is passed through the tube 1, the float 2 will tend to rise. Liquid flowing into the basket 3 through the small hole 7 will allow the float 2 to move upwardly out of the basket 3, guided by the connecting/guide rods 4 until the chamfered walls 8 engage the exit orifice 6, blocking it off and halting the flow of liquid through the tube 1.

Referring to FIG. 2, the various parts of the apparatus shown are numbered as in FIG. 1, the whole apparatus having been in effect inverted. Liquid flowing downwardly through the tube 1 in the direction of the arrow will, if its density is within the predetermined range, flow round the basket 3, over the chamfered side walls 8 of the float 2 between the connecting/guide rods 4, and out through the exit orifice 6. The float 2 will remain floating within the basket 3. If a liquid, the density of which is less than the predetermined range, is now passed through the tube 1, the float 2 will tend to sink. Liquid flowing into the basket 3, through the small hole 7, will allow the float 2 to move downwardly, out of the basket 3, guided by the connecting/guiding rods 4, until the chamfered walls 8 engage the exit orifice or outlet 6, blocking it off and halting the flow of liquid through the tube 1.

FIG. 3 is a cross-sectional view of the arragement shown in FIG. 1 at the line A—A$^1$, the parts being numbered as in FIG. 1.

The preferred apparatus, illustrated in FIG. 4, comprises a first body member 40 carrying two vertical tubes 41 and 51. One of the vertical tubes 41 is a vertical tube, as shown in FIG. 1, through which liquid flows in an upward direction after entering through an orifice or inlet 49 in the first body member 40. This tube 41 contains a float 42, seated loosely in a basket 43, suspended by means of connecting/guide rods 44 from a horizontal disc 45, which sealingly contacts the end of the tube 41 and the first body member 40, and which has a central hole 46 which functions as the exit orifice or outlet of the tube 41. A small hole 47 is provided in the base of the basket 43 to allow liquid to enter when the float 42 moves upwardly within it. The float 42 is provided with a chamfered upper section 48 to facilitate a good seal between it and the exit orifice 46. The second vertical tube 51 is a vertical tube, as shown in FIG. '2, through which liquid flows in a downward direction after entering through an orifice or inlet 59 in the first body member 40. This tube contains a float 52, seated loosely in a basket 53, supported by means of connecting/guide rods 54 on a horizontal disc 55. The disc 55 sealingly contacts the end of the tube 51 and the first body member 40, and has an exit orifice or outlet 56. A small hole 57 is provided in the base of the basket 53 to allow liquid to enter when the float 52 moves downwardly within it. The float 52 is provided with a chamfered lower section 58 to facilitate a good seal between it and the exit orifice 56.

Also incorporated into the first body member 40 of the apparatus, illustrated in FIG. 4, is a non-return valve comprising a perforated disc 60 fitting into a space in the first body member 40, just following the exit orifice 56 of the second vertical tube 51. A second solid disc 61 is slidably mounted below the disc 60 on an extension 62 of the first disc 60. The second disc 61 is disposed to be urged upwardly towards the first disc by a spring 63, and thus, to block off the perforations in the first perforated disc 60.

A second body member 70 is mounted above the first 40, and comprises a relatively large hollow container having incorporated therein a float 71. The float is supported by an arm 72, which is pivoted with a pin 73 from the bracket 74 mounted on the inside of the second body member 70. The arm 72 actuates an air-separation valve comprising a disc 82 mounted on a spindle 80, whose weight is sufficient to cause it to drop and open the vent 83. The disc 82 is moved upward to close the vent 83 by the float 71 rising to lift the arm 72.

In operation, liquid flows into the apparatus through inlet orifice 49 in the first body member 40, and up the first vertical tube 41. The density of the float 42 in that tube is selected so that while the density of the flowing liquid is below a predetermined value, it will have a negative buoyancy and remain within the basket 43. The flow of liquid over the chamfered area 48 of the float 42 tends to reinforce this effect. Liquid flows out of the first tube 41 through the outlet orifice 46 into the relatively large hollow second body member 70. Provided that there is no air in the system, the second body member is full of liquid and the float 71 is forced upwardly by its buoyancy, forcing the arm 72 to press against the spindle 80, and hold the disc 82 tightly against the vent 83, keeping the latter closed off.

From the inside of the second body member 70, liquid flows through the second inlet orifice 59 and down the second vertical tube 51. The density of the float 52 in that tube is selected so that while the density of the flowing liquid is above a predetermined value, it will have a positive buoyancy and remain floating within the basket 53. The flow of liquid over the chamfered area 58 of the float 52 tends to reinforce this effect. Liquid flows out of the second vertical tube through the outlet orifice 56 and passes through the non-return valve incorporated into the first body member 40 at that point. Liquid flows through the perforated disc 60 and over the solid disc 61, urging this downwardly along the extension 62 against the action of the spring 63.

Entry into the apparatus of liquid, having a density greater than the predetermined value, will cause the float 42 in the first vertical tube 41 to rise out of its basket 43, and guided by the connecting/guide rods 44, to enter and seal off the outlet orifice 46, shutting off the flow of liquid through the system. Entry into the apparatus of liquid, having density lower than the predetermined value, will cause the float 42 in the first vertical tube 41 to be more firmly held in its basket 43, but will cause the float 52 in the second vertical tube 51 to move downwardly out of its basket 53, and guided by the connecting/guide rods 54, to enter and seal off the outlet orifice 56, shutting off the flow of liquid through the system.

Air, or any other dissolved or included gas, entering the system will tend to gather within the relatively large hollow second body member 70, this being the highest place in the system. The air will form a layer collected above the liquid in the second body member 70 and the liquid level will fall. The float 71, floating on the liquid surface, falls causing the arm 72 to pivot on the pin 73, and allowing the spindle 80 to drop to open the vent 83, allowing air or gas to exhaust past. As the air or gas escapes, so more liquid will take its place and the float 71 will be raised again to close the vent 83.

If, for any reason, for example as a result of cessation of flow through the system, flow through the apparatus is reversed; the action of the spring 63 in the non-return valve is reinforced by the reverse liquid flow and the solid disc 61 is quickly closed against the perforated one, blocking off the outlet 56 from the second vertical tube 51, and shutting off any flow of liquid through the system up into that tube 51.

In FIG. 5, a density monitoring apparatus, as shown in FIG. 4, comprises two vertical tubes 102 and 101, floats 100 and 103, an air separation valve 104, and a non-return valve 105. The density monitoring apparatus is connected by means of an inlet 106 and an outlet 107 to a servo-operated valve. The servo-operated valve comprises a body member 110, containing a double-acting piston 111 slidably mounted within a valve member 115, urged by a spring 112 against the flow of liquid through the body member 110, as indicated by the arrow towards a sealing face 114. A central passageway 108 is provided centrally through the piston 111, and communicates with a first chamber 116 within the valve member 115. The inlet 106 also communicates with this part 116 of the inside of the valve member 115. Holes 120 are provided in the circumference of the valve member 115, communicating between the inside of the body member 110 and a second chamber 117 within the valve member 115. The outlet 107 feeds directly back into the inside of the body member 110.

When a liquid enters the body member 110, the greatest part of it flows past the outside of the valve member 115 and continues on its way. A small portion of the flow, however, passes through the central passageway 108 in the piston 111, and enters the first chamber 116 within the valve member 115 from where it flows through the inlet 106 into the density monitoring apparatus. Provided that the density of the liquid flowing within the system is within the predetermined range, liquid entering the density monitoring apparatus will flow upwardly through the first vertical tube 102, downwardly through the second vertical tube 101, and then out through the outlet 107 to the inside of the body member 110. If the density of the liquid is outside the predetermined range, one or other of the floats 100 or 103 will move into its cooperating outlet orifice and cut off the flow of liquid through the density monitoring apparatus. When the flow of liquid through the inlet 106 is stopped, liquid flowing into the first chamber 116 can no longer pass through the density monitoring apparatus to return to the liquid flowing through the body member 110. The pressure level of the liquid inside the first chamber 116 increases and assists the spring 112 to urge the piston 111 against the flow of incoming liquids towards the sealing face 114. Liquid in the second chamber 117 is forced out through the holes 120 in the circumference of the valve member 115 into the inside of the body member 110. The piston 111 is quickly pushed against the sealing face 114, closing off the main flow of liquid through the system.

It will be clear that a pressure differential will be required across the piston 111 for the servo-operated valve to open again and the flow to commence. If the fuel system comprising the above-mentioned system is pressure-fed, i.e., the liquid is pumped into the body member 110, then opening of the valve, i.e., overcoming the pressure caused by the spring 112, will be no particular problem. This situation differs in the case of the liquid being gravity-fed. Because of the low pressure in gravity feed systems, the pressure differential is inevitably low and a weaker spring 112 is necessary to obtain a satisfactory pressure balance. However, a lower spring force may be insufficient to close the valve, which is unacceptable in view of the fact that the valve should fail safe, i.e., tends to close.

In order to overcome this problem, it may be possible to make use of a variable rate spring or a mechanical lever.

A very convenient way of reopening the valve is to apply a suction to the air bleed port 104 of the monitoring apparatus. Because of the non-return valve 105 in the outlet 107 of the monitoring apparatus, the suction is transmitted through the inlet tube 106 of said apparatus to the first chamber 116 of the servo-operated valve. The inlet 108 to this chamber 116 is restricted by an orifice so that a partial vacuum or a pressure below the atmospheric pressure is pulled on this chamber 116. This vacuum combined with the pressure head at the inlet to the valve causes the piston 111 to be pushed against the pressure of the spring 112, and thus, the main flow of liquid to start again. Once the servo-operated valve is opened and liquid is flowing, a correct balance of the pressures is set up, and the said valve remains open without the application of further suction until such time as the main flow ceases.

While the above discription relates to the use of the invention to monitor changes in density of similar fluids, i.e., aviation turbine fuel and gasoline, it can also be used to monitor density changes resulting from entirely different fluids. For example, the monitor can be used to control the draining of water from a storage tank containing petroleum products. The monitor can also be used to control product pipelines handling different products. Likewise, different type servo-valves, for example pneumatically or electrically operated valves, may be used.

It will be understood that, although the examples show vertical tubes, a system according to the invention will also operate with a tube or tubes being placed at an angle other than 90° with the horizontal plane.

What we claim is:

1. A system for monitoring the density and preventing the passage of a liquid with a density outside a predetermined range having at least two parts arranged in a substantially vertical manner where each part comprises:
   a body having an inlet and an outlet, and adapted for the passage of said liquid therethrough; and
   a movable member having a weight/volume ratio substantially equal to said density, which member is adapted to move freely within said body between its outlet and its inlet, and is also adapted sealingly to engage with said outlet;
   where the outlet of the first part communicates with the inlet of the second part, whereby a flow of liquid is made to pass through the substantially vertically placed parts in such a manner that the flowing liquid passes upwardly through one and downwardly through the other part, while the movable member in the one part will close off its outlet when the density of the flowing liquid increases beyond the predetermined range and the movable member in the other part will close off its outlet when the density of the flowing liquid decreases beyond the predetermined range.

2. A system as claimed in claim 1, wherein said body is of substantially tubular shape.

3. A system as claimed in claim 2, and, in addition, a guide member for the movable member disposed inside said body, said guide member being disposed so that the movable member cannot engage with the inlet.

4. A system as claimed in claim 1, wherein the flow of liquid passing through the body is only a proportion of a main flow of liquid and whereby the closing of an outlet by means of a movable member is used to generate a signal for controlling the main flow.

5. A system as claimed in claim 1, wherein the parts of said system are arranged in a single body member.

6. An apparatus for monitoring the density of a flowing liquid stream comprising:
   a body member having two vertical, parallel, elongated passageways formed therein, said passageways terminating in top and bottom openings formed in said body member;
   a cup-shaped member disposed to enclose the top openings of both of said passageways, said cup-shaped member being sealed to said body member;
   vent means disposed to vent said cup-shaped member, said vent means being responsive to the liquid level in said cup-shaped member;
   a float means disposed in each of said passageways, said float means having a density substantially equal to the density of the liquid;
   support and guide means disposed in each passageway, said float means being restrained by said support and guide means to travel in a vertical direction, and in addition, one of said support and guide means preventing its associated float from falling to the bottom of one passageway, said other support and guide means preventing its associated float from rising to the top of the other passageway, whereby the float in said one passageway can rise to close the top opening of said one passageway and the float in said other passageway can fall to close the bottom opening in said other passageway;
   means for establishing a flow of said liquid upwardly through said one passage and downwardly through said other passageway; and
   means responsive to the closing of either the top or bottom openings by said floats to stop the flow of liquid.

* * * * *